US009131576B2

(12) United States Patent
Nishio et al.

(10) Patent No.: US 9,131,576 B2
(45) Date of Patent: *Sep. 8, 2015

(54) LIGHT SOURCE DEVICE

(71) Applicant: OLYMPUS CORPORATION, Tokyo (JP)

(72) Inventors: Masahiro Nishio, Hachioji (JP); Eiji Yamamoto, Musashimurayama (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/148,938

(22) Filed: Jan. 7, 2014

(65) Prior Publication Data
US 2014/0125231 A1    May 8, 2014

Related U.S. Application Data

(63) Continuation of application No. PCT/JP2012/067723, filed on Jul. 11, 2012.

(30) Foreign Application Priority Data

Jul. 11, 2011    (JP) .................. 2011-153207

(51) Int. Cl.
*F21V 7/04* (2006.01)
*H05B 33/08* (2006.01)
(Continued)

(52) U.S. Cl.
CPC ........ *H05B 33/0845* (2013.01); *A61B 1/00059* (2013.01); *A61B 1/0638* (2013.01);
(Continued)

(58) Field of Classification Search
CPC ................................. G02B 6/00; F21K 9/52
USPC ........... 362/552–552, 84, 551, 581, 313, 555, 362/556
See application file for complete search history.

(56) References Cited

U.S. PATENT DOCUMENTS

2007/0010712 A1    1/2007  Negishi
2009/0237011 A1*   9/2009  Shah et al. ............... 315/312
(Continued)

FOREIGN PATENT DOCUMENTS

EP    2 301 414 A1    3/2011
JP    2006-061685 A   3/2006
(Continued)

OTHER PUBLICATIONS

International Search Report dated Sep. 18, 2012 issued in PCT/JP2012/067723.
(Continued)

*Primary Examiner* — Minh D A
(74) *Attorney, Agent, or Firm* — Scully, Scott, Murphy & Presser, PC

(57) ABSTRACT

A light source device includes a light source unit configured to emit primary light and an illumination unit configured to optically convert the primary light to secondary light and then emit the secondary light. The light source device further includes a connector configured to allow the light source unit and the illumination unit to be attached to and detached from each other. Furthermore, the light source device includes an information transmitter configured to transmit illumination unit information to the light source unit, the illumination unit information being information regarding the illumination unit.

17 Claims, 4 Drawing Sheets

(51) Int. Cl.
*A61B 1/06* (2006.01)
*A61B 1/00* (2006.01)
*G02B 23/24* (2006.01)

(52) U.S. Cl.
CPC .......... *A61B1/0669* (2013.01); *G02B 23/2461* (2013.01); *G02B 23/2476* (2013.01); *H05B 33/086* (2013.01)

(56) References Cited

U.S. PATENT DOCUMENTS

2010/0113877 A1   5/2010   Suzuki
2014/0022810 A1*  1/2014   Ito et al. .................. 362/551
2014/0146559 A1*  5/2014   Ito et al. .................. 362/583

FOREIGN PATENT DOCUMENTS

| JP | 2006-158716 A | 6/2006 |
| JP | 2006-173324 A | 6/2006 |
| JP | 2009-043668 A | 2/2009 |

OTHER PUBLICATIONS

Extended Supplementary European Search Report dated Apr. 1, 2015 from related European Application No. 12 81 1235.6.

* cited by examiner

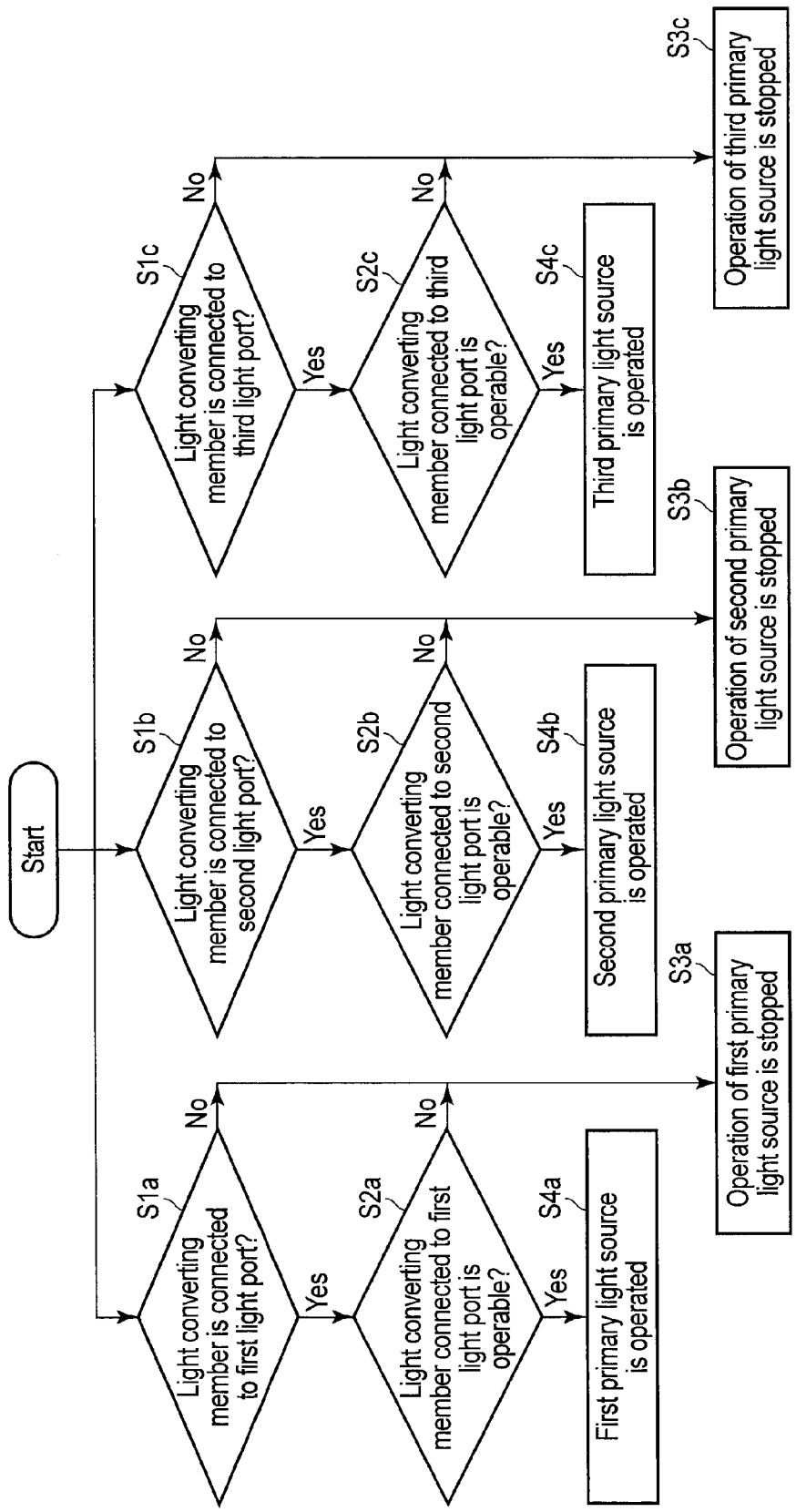
F I G. 4

LIGHT SOURCE DEVICE

CROSS-REFERENCE TO RELATED APPLICATIONS

This application is a Continuation Application of PCT Application No. PCT/JP2012/067723, filed Jul. 11, 2012 and based upon and claiming the benefit of priority from the prior Japanese Patent Application No. 2011-153207, filed Jul. 11, 2011, the entire contents of which are incorporated herein by reference.

BACKGROUND OF THE INVENTION

1. Field of the Invention

The present invention relates to a light source device which radiates illumination light.

2. Description of the Related Art

A related art of a light source device which radiates illumination light is disclosed in, for example, US2005/0107032A1. A light emitting device suggested in US2005/0107032A1 is a combination of light emitting units each including a laser light source, a light guide which includes an optical fiber, and a wavelength converting member. In a first light emitting unit of this light emitting device, a blue laser light source is provided at the proximal end of the light guide which includes the optical fiber, and the wavelength converting member is provided at the distal end of the light guide. Laser light emitted from the blue laser light source is guided to the distal end by the light guide, and the wavelength of the laser light is converted by the wavelength converting member at the distal end of the light guide. Further, a laser light source having a wavelength shorter than that of blue, a light guide, and a wavelength converting member are used to constitute a second light emitting unit. US2005/0107032A1 discloses that the first light emitting unit and the second light emitting unit are combined to constitute the light emitting device so that color rendering properties are improved as compared to those in the case of the single first light emitting unit.

Recently, in connection with light source devices used for observation in, for example, endoscopes, efforts have been made to improve the visibility of an observation target by properly selecting brightness, a peak wavelength, an emitted color, i.e. a spectrum shape, a radiation angle, and an emission pattern shape of illumination light depending on the purpose of observation.

In the light source device according to the conventional art in US2005/0107032A1, it is necessary to prepare different kinds of light emitting units in the body of the light source device, and adjust the combination of the light emitting units to be used to a purpose, in order to obtain illumination light suited to the purpose. However, the preparation of a large number of light emitting units in the body of the light source device is not preferable in respect of costs and storage locations.

BRIEF SUMMARY OF THE INVENTION

The present invention has been made in view of the foregoing circumstances. An object of the invention is to provide a light source device capable of radiating various kinds of illumination light suited to use.

According to an aspect of the invention, there is provided alight source device comprising:
a light source unit configured to emit primary light;
an illumination unit configured to optically convert the primary light to secondary light and then emit the secondary light;
a connector configured to allow the light source unit and the illumination unit to be attached to and detached from each other; and
an information transmitter configured to transmit illumination unit information to the light source unit, the illumination unit information being information regarding the illumination unit.

According to the present invention, it is possible to provide a light source device capable of radiating various kinds of illumination light suited to use.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a flowchart illustrating the operation of a control circuit of the light source device according to the first embodiment;

DETAILED DESCRIPTION OF THE INVENTION

First Embodiment (Configuration)

Figure 1:
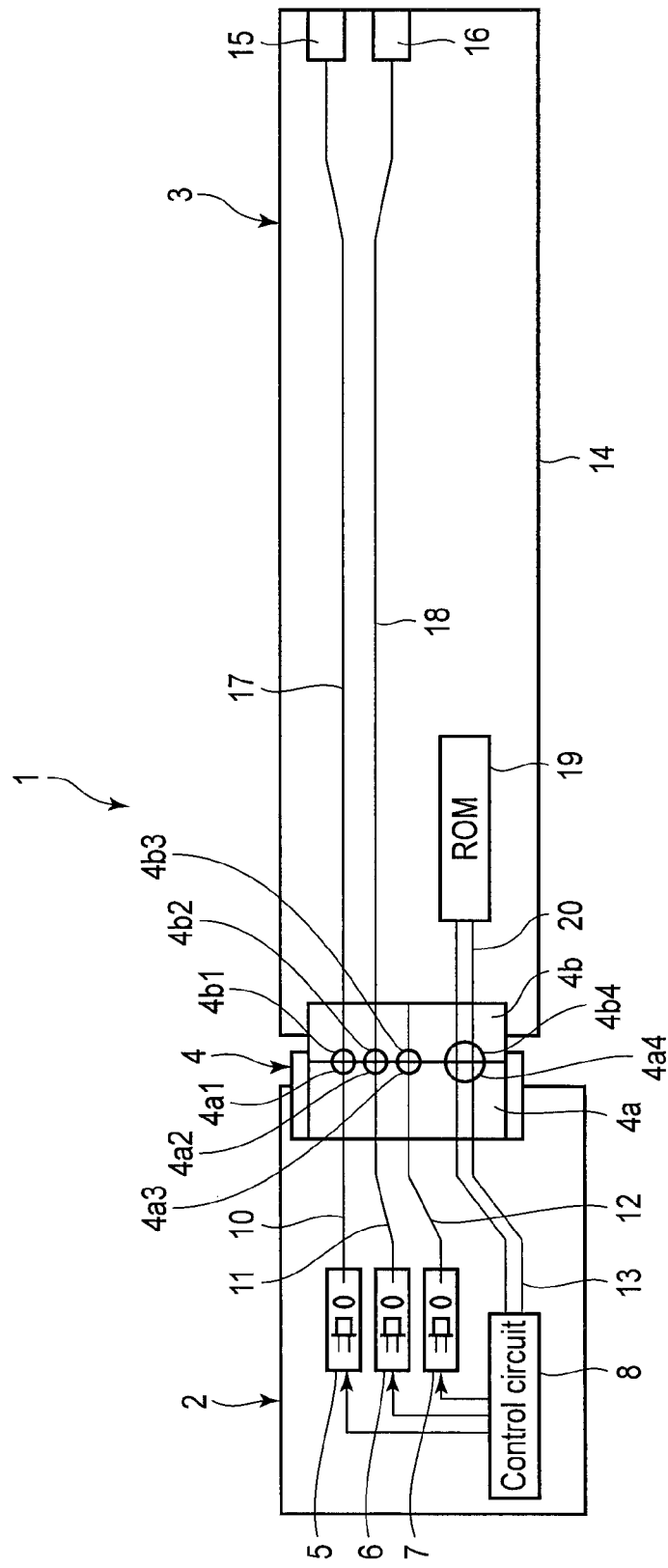
FIG. 1 is a schematic diagram showing the overall configuration of a light source device according to a first embodiment of the present invention.

FIG. 1 to FIG. 4 show a first embodiment of the present invention. FIG. 1 is a schematic diagram showing the overall configuration of a light source device 1 according to the first embodiment. As shown in FIG. 1, the light source device 1 according to the present embodiment includes a light source unit 2, an illumination unit 3, and a connector 4 which connects the above units.

The light source unit 2 has three primary light sources (a first primary light source 5, a second primary light source 6, and a third primary light source 7), a control circuit 8, and an informer 9 (see FIG. 2) which informs a user. The first primary light source 5, the second primary light source 6, and the third primary light source 7 are formed by, for example, semiconductor laser light sources which are at least partly different in the characteristics of emitted primary light (emitted light functions such as a maximum light output, a peak wavelength, and a spectrum shape of the primary light). Here, for example, the first primary light source 5 is formed by a blue laser light source. The second primary light source 6 is formed by a laser light source having a wavelength shorter than that of the blue laser light source. The third primary light source 7 is formed by a laser light source different in wavelength from the first primary light source 5 and the second primary light source 6.

The control circuit 8 is connected to the first primary light source 5, the second primary light source 6, the third primary light source 7, and the informer 9 via signal lines (or by wireless communication). The outputs of the first primary light source 5, the second primary light source 6, and the third primary light source 7 are controlled by a control signal from the control circuit 8. The output of the informer 9 is also controlled by a control signal from the control circuit 8.

One end of a first optical fiber 10 is connected to the first primary light source 5. Similarly, one end of a second optical fiber 11 is connected to the second primary light source 6, and one end of a third optical fiber 12 is connected to the third primary light source 7.

The connector 4 has a first connector portion 4a connected to the side of the light source unit 2, and a second connector portion 4b connected to the side of the illumination unit 3. The first connector portion 4a is provided with three light connection light ports (a first light port 4a1, a second light port 4a2, and a third light port 4a3) to have optical connection, and one electric connection electric port 4a4 to have electric connection.

The other end of the first optical fiber 10 is connected to the first light port 4a1 of the first connector portion 4a. Similarly, the other end of the second optical fiber 11 is connected to the second light port 4a2, and the other end of the third optical fiber 12 is connected to the third light port 4a3. Moreover, the control circuit 8 is connected to the electric port 4a4 of the first connector portion 4a via electric signal lines 13.

The second connector portion 4b of the connector 4 is provided with three light connection light ports (a first light port 4b1, a second light port 4b2, and a third light port 4b3), and one electric connection electric port 4b4.

Figure 3:
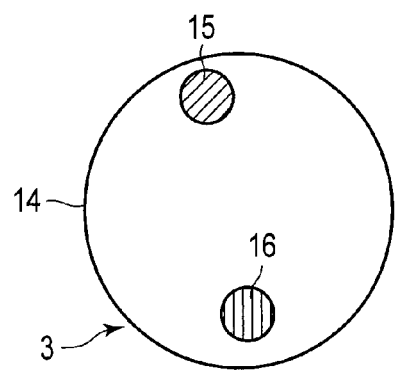
FIG. 3 is a front view of essential parts showing the location of a first light converting member source and a second light converting member in the distal end face of the illumination unit of the light source device according to the first embodiment.

The illumination unit 3 has, for example, a cylindrical unit body 14. The second connector portion 4b is provided at the proximal end of the unit body 14. More than one light converting member, in the present embodiment as shown in FIG. 3, two light converting members (a first light converting member 15 and a second light converting member 16) are mounted in the end face at the distal end of the unit body 14. The light converting member converts at least one of the peak wavelength, spectrum shape, and radiation angle of primary light and then emits the light as illumination light (secondary light). That is, the two light converting members (the first light converting member 15 and the second light converting member 16) have a light converting function to receive the primary light emitted from one of the three primary light sources (the first primary light source 5, the second primary light source 6, and the third primary light source 7), and convert the primary light to secondary light and then emit the secondary light. The secondary light emitted by the first light converting member 15 and/or the second light converting member 16 is emitted as illumination light from the end face of the illumination unit 3.

One end of a first optical fiber 17 is connected to the first light converting member 15. Similarly, one end of a second optical fiber 18 is connected to the second light converting member 16. The other end of the first optical fiber 17 is connected to the first light port 4b1 of the second connector portion 4b, and the other end of the second optical fiber 18 is connected to the second light port 4b2. Nothing is connected to the third light port 4b3 of the second connector portion 4b.

The unit body 14 of the illumination unit 3 has a ROM 19 as a recording medium to record illumination unit information regarding the illumination unit 3. The following information is stored in the ROM 19 as the illumination unit information: information regarding whether the light converting members (the first light converting member 15 and the second light converting member 16) are connected to the three light connection light ports (the first light port 4b1, the second light port 4b2, and the third light port 4b3), and information regarding the characteristics (a maximum light output, a peak wavelength, and a spectrum shape) of the primary light necessary for the operation of the light converting members (the first light converting member 15 and the second light converting member 16) connected to the three light connection light ports (the first light port 4b1, the second light port 4b2, and the third light port 4b3). This ROM 19 is connected to the electric port 4b4 of the second connector portion 4b via electric signal lines 20.

The first connector portion 4a and the second connector portion 4b of the connector 4 are configured to be attachable to and detachable from each other. When the first connector portion 4a and the second connector portion 4b are connected to each other, the three light connection light ports (the first light port 4a1, the second light port 4a2, and the third light port 4a3) and the one electric connection electric port 4a4 are respectively connected to the three light connection light ports (the first light port 4b1, the second light port 4b2, and the third light port 4b3) and the one electric connection electric port 4b4 that correspond. At the same time, the electric port 4a4 of the first connector portion 4a is connected to the electric port 4b4 of the second connector portion 4b, so that the ROM 19 of the illumination unit 3 is connected to the control circuit 8 of the light source unit 2, and the contents (illumination unit information) of the ROM 19 can be read by the control circuit 8 via the electric ports 4a4 and 4b4 of the connector 4. Thus, the electric ports 4a4 and 4b4 of the connector 4 function as an information transmitter to transmit the illumination unit information to the light source unit 2.

The control circuit 8 has a storage 8a such as a ROM to store information. The storage 8a has information regarding the characteristics of the primary light sources (the first primary light source 5, the second primary light source 6, and the third primary light source 7) in the light source unit 2 connected to the three light connection light ports (the first light port 4a1, the second light port 4a2, and the third light port 4a3) of the connector 4.

(Functions)

Figure 2:
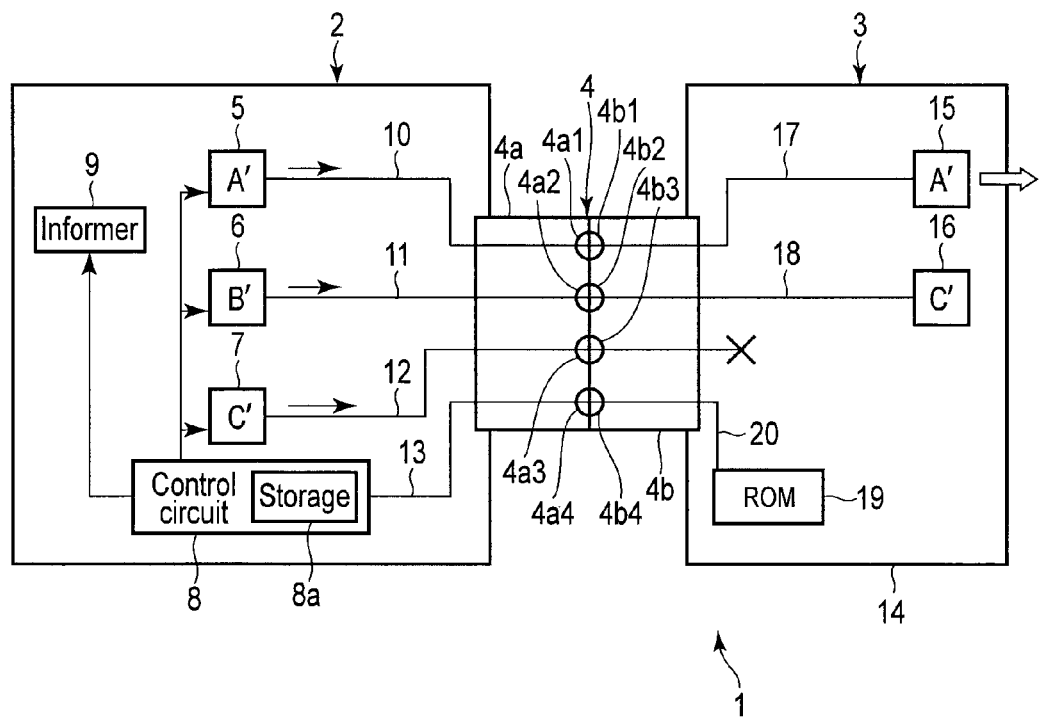
FIG. 2 is a schematic configuration diagram of essential parts showing the connection of a light source unit and an illumination unit in the light source device according to the first embodiment.

Now, the functions of the above configuration are described. When the light source device 1 according to the present embodiment is used, the first connector portion 4a of the light source unit 2 is connected to the second connector portion 4b of the illumination unit 3. When the light source unit 2 and the illumination unit 3 are connected to each other, the electric port 4a4 of the first connector portion 4a is connected to the electric port 4b4 of the second connector portion 4b as shown in FIG. 2, so that the ROM 19 of the illumination unit 3 is connected to the control circuit 8 of the light source unit 2. In this condition, the control circuit 8 can read the information stored in the ROM 19 via the electric ports 4a4 and 4b4 of the connector 4 serving as the information transmitter.

The control circuit 8 then operates the three primary light sources (the first primary light source 5, the second primary light source 6, and the third primary light source 7) in the light source unit 2 to obtain illumination light. However, the illumination unit information is read from the ROM 19 in advance. As described above, this illumination unit information includes the information regarding whether the light converting members are connected to the light ports (the first light port 4b1, the second light port 4b2, and the third light port 4b3) of the illumination unit 3 corresponding to the light ports (the first light port 4a1, the second light port 4a2, and the third light port 4a3) to which the target primary light source is connected, and the information regarding the characteristics of the primary light necessary for the operation of the light converting members.

In this instance, the control circuit 8 performs the operation shown in a flowchart of FIG. 4. That is, first, in step S1a, step S1b, and step S1c, the control circuit 8 determines whether the light converting members are connected to the first light port 4b1, the second light port 4b2, and the third light port 4b3 of the illumination unit 3. The control circuit 8 makes this determination in accordance with the read illumination unit information.

When determining here that the light converting members are connected, the control circuit 8 moves to the following step S2a, step S2b, and step S2c. In contrast, when determining that the light converting members are not connected, the control circuit 8 moves to the following step S3a, step S3b, and step S3c. In step S3a, the first primary light source 5 is kept inactive. Similarly, the second primary light source 6 is kept inactive in step S3b, and the third primary light source 7 is kept inactive in step S3c.

In step S2a, step S2b, and step S2c, the control circuit 8 determines whether the characteristics of the primary light operable in the light converting members are suited to the characteristics of the primary light sources, that is, whether the light converting members can be operated by the primary light sources. The control circuit 8 makes this determination in accordance with the information regarding the characteristics of the primary light sources (the first primary light source 5, the second primary light source 6, and the third primary light source 7) in the light source unit 2 stored in the storage 8a, for example, the ROM provided in the control circuit 8.

When determining here that the characteristics are suited or the light converting members can be operated, the control circuit 8 moves to the following step S4a, step S4b, and step S4c. In contrast, when determining that the characteristics are not suited or the light converting members cannot be operated, the control circuit 8 moves to the following step S3a, step S3b, and step S3c. In step S4a, the first primary light source 5 is operated. Similarly, the second primary light source 6 is operated in step S4b, and the third primary light source 7 is operated in step S4c.

Here, the operation of the control circuit 8 according to the example in FIG. 2 is described. In an example shown FIG. 2, the three primary light sources (the first primary light source 5, the second primary light source 6, and the third primary light source 7) are located on the side of the light source unit 2, and the two light converting members (the first light converting member 15 and the second light converting member 16) are mounted on the side of the illumination unit 3. Here, in this example, the characteristics of the first light converting member 15 are suited to the first primary light source 5, and the characteristics of the second light converting member 16 are not suited to the second primary light source 6.

When the first connector portion 4a of the light source unit 2 is connected to the second connector portion 4b of the illumination unit 3 in this example, the first light port 4a1 on the side of the light source unit 2 is connected to the first light port 4b1 on the side of the illumination unit 3 which is connected to the first light converting member 15. In this instance, step S1a results in "Yes", and the control circuit 8 moves to step S2a. Moreover, the first primary light source 5 satisfies the characteristics of the primary light necessary for the operation of the first light converting member 15. Therefore, step S2a results in "Yes", and the control circuit 8 moves to step S4a. Consequently, the control circuit 8 permits the operation of the first primary light source 5.

The second light port 4a2 on the side of the light source unit 2 is connected to the second light port 4b2 on the side of the illumination unit 3 which is connected to the second light converting member 16. In this instance, step S1b results in "Yes", and the control circuit 8 moves to step S2b. In this case, the second primary light source 6 does not satisfy the characteristics of the primary light necessary for the operation of the second light converting member 16. Therefore, step S2b results in "No", and the control circuit 8 moves to step S1b. Consequently, the control circuit 8 does not permit the operation of the second primary light source 6.

No light converting member is connected to the third light port 4b3 on the side of the illumination unit 3 which is connected to the third light port 4a3 on the side of the light source unit 2. In this instance, step S1c results in "No", and the control circuit 8 moves to step S3c. Consequently, the control circuit 8 does not permit the operation of the third primary light source 7.

Therefore, in the example in FIG. 2, the first primary light source 5 alone operates on the side of the light source unit 2. The laser light (primary light) emitted from the first primary light source 5 is then guided to the first light converting member 15 via the first optical fiber 10 on the side of the light source unit 2, the first light port 4a1 of the first connector portion 4a, the first light port 4b1 of the second connector portion 4b, and the first optical fiber 17 on the side of the illumination unit 3 in turn. The primary light received by the first light converting member 15 is converted to secondary light and then radiated. The secondary light radiated from the first light converting member 15 is radiated to the outside as illumination light from the end face of the illumination unit 3.

Although the determination processing is performed in parallel in the present embodiment described, the determination processing may be sequentially performed.

When the illumination unit information cannot be read from the ROM 19, the control circuit 8 does not permit the operation of the primary light source in principle. Moreover, the primary light source to be operated may be decided by user operation. In order to know which of the illumination units 3 are connectable to the light source unit 2, the control circuit 8 may use the informer 9 to inform the user of the information regarding the primary light sources mounted on the light source unit 2.

Alternatively, the control circuit 8 may use the informer 9 to inform the user of the illumination unit information regarding the illumination unit 3 read from the ROM 19, that is, the characteristics of the primary light necessary for the operation of the light converting member(s). The control circuit 8 may also use the informer 9 to show a combination of an operable light source and the light converting member to the user. Alternatively, the control circuit 8 may use the informer 9 to indicate the name of the illumination light obtained by the combination. Alternatively, the control circuit 8 may inform the user of the primary light source in the light source unit 2 which is prohibited from operating.

(Advantageous Effects)

Accordingly, the configuration described above has the following advantageous effects. That is, in the present embodiment, it is possible to obtain the light source device 1 in which the light source unit 2 and the illumination unit 3 are attachable to and detachable from each other. As a result, illumination light suited to the use can be obtained by a proper combination of the light source unit 2 and the illumination unit 3. That is, in the present embodiment, when the light source unit 2 and the illumination unit 3 are connected to each other, the electric port 4a4 of the first connector portion 4a is connected to the electric port 4b4 of the second connector portion 4b, so that the ROM 19 of the illumination unit 3 is connected to the control circuit 8 of the light source unit 2. The information transmitter including the electric ports 4a4 and 4b4 of the connector 4 is provided so that the illumination unit information as the contents of the ROM 19 can be read by the control circuit 8. In accordance with this illumination unit information, the control circuit 8 properly selects and combines the two light converting members (the first light converting member 15 and the second light converting member 16) of the illumination unit 3 for the three primary light sources (the first primary light source 5, the second primary light source 6, and the third primary light source 7) mounted on the light source unit 2. Thus, the light source device 1 can switch the optical characteristics of the illumination light (secondary light) to be emitted. If this combination is properly selected, it is possible to obtain the light source device 1 in which the light source unit 2 capable of radiating various kinds of light can be located with high spatial efficiency.

As described above, the illumination unit information is transmitted from the illumination unit 3 to the light source unit 2. When determining in accordance with this illumination unit information that the connection, via the ports of the connector 4, of the three primary light sources (the first primary light source 5, the second primary light source 6, and the third primary light source 7) of the light source unit 2 and the two light converting members (the first light converting member 15 and the second light converting member 16) mounted on the illumination unit 3 is a proper combination, the control circuit 8 permits the output of the light sources connected to the ports. This ensures the operation of the light source device 1. As a result, it is possible to automatically obtain the optimum and safe illumination light without the operation by the operator.

[Modification]

Although the control circuit 8 is electrically connected to the ROM 19 in the present embodiment, the control circuit 8 may be optically connected to the ROM 19 by the conversion from electricity to light. In this case, the port in the connector 4 is a light port alone. In the configuration according to the present embodiment, the illumination unit information is stored in the ROM 19. However, the illumination unit information may be recorded on the side of the illumination unit 3 of the connector 4 by the use of a reflection pattern such as a bar code or depressions and projections, and a mechanism to optically or mechanically read this reflection pattern may be disposed on the side of the light source unit 2.

Another function such as an image acquiring function may be additionally provided along with the illumination unit 3 for use with the light source device 1 according to the present embodiment. In this case, information regarding the additionally provided image acquiring function is also stored in the ROM 19, and the control circuit 8 may be configured to control the primary light source in consideration of the combination of the light converting member and the primary light source so that illumination light necessary for the operation of the image acquiring function can be obtained in combination with the illumination unit information.

When there is a characteristic that can be adjusted by the operation of the primary light source among the characteristics of the primary light source, whether the primary light source is operable may be determined by whether the operable range of the light converting member is included in the adjustable range of the primary light source. It is also possible to have a configuration which adjusts the operation of the primary light source within the range of the characteristics necessary for the operation of the light converting member and operates the primary light source.

For example, the adjustable range of the characteristics of the primary light source is 500 mW or less, and the operable range of the light converting member is 0 mW to 400 mW. In this case, the adjustable range of the characteristics of the primary light source includes the operable range of the light converting member, the light converting member is determined to be operable. The primary light source is then operated so that its output light intensity is adjusted within a range of 0 mW to 400 mW.

The primary light source may include a wavelength variable light source, and the determination of its operability and the wavelength adjustment may be performed in accordance with a spectrum shape necessary for the operation.

Information regarding a method of varying the intensity of the primary light may be stored as the illumination unit information. The varying method is, for example, electric current variation or pulse width modulation. The varying method and a corresponding condition of the primary light such as an operable light intensity range may be stored as a pair.

It is also possible to have a configuration which finds operable illumination functions from the combination of the primary light sources and the light converting members in accordance with the illumination unit information, and indicates, to the user, the kinds and names of the operable illumination functions before or during the operation of the light sources. In this case, the user can recognize which illumination function is usable.

It is also possible to have a configuration which finds illumination functions that are not permitted to operate from the combination of the primary light sources and the light converting members in accordance with the illumination unit information, and indicates, to the user, the kinds and names of the illumination functions that are not permitted to operate before or during the operation of the light source.

In case of emergency, for example, when light cannot be generated because of a serious failure in one of the primary light source and the light converting member that are a combination to be originally operated, another combination of the primary light source and the light converting member which is generally not permitted to generate light may be specially permitted to generate light even when this light has an unsuitable wavelength as long as the illumination light from the emission end is within a safe range. To this end, a condition which does not provide the optimum primary light but which allows the emission of illumination light with safety may be stored in the ROM 19 as the illumination unit information.

No light converting member is connected to the third light port 4b3 of the illumination unit 3. In this case, the third light port 4b3 on the side of the illumination unit 3 may not be provided, that is, may be a blind port. In this case, processing may be performed on the assumption that no light converting member is connected to this port.

In the embodiment described above, the optical information regarding the light converting member of the illumination unit 3 is recorded in the ROM 19 as the illumination unit information. However, mechanical information or thermal information may be stored as the illumination unit information for the determination of the suitability for operation.

For example, the control circuit 8 controls the operations of the primary light sources by determining whether mechanical connection is ensured in accordance with mechanical information regarding the shape of the connector 4 between the first connector portion 4a of the light source unit 2 and the second connector portion 4b of the illumination unit 3. Alternatively, the control circuit 8 may control the operations of the primary light sources by determining, in accordance with mechanical information regarding the shape of the light source unit 2, whether the shape of the illumination unit 3 is suitable for the use of the light source device 1.

For example, when the illumination unit 3 is conditioned to operate with a predetermined heat quantity or less, the control circuit 8 may be configured to control, in accordance with the information regarding this thermal restriction, the output light intensities of the primary light sources so that the heat quantity satisfies this condition.

Optical characteristic information regarding primary light transmission in each port may be stored in the ROM 19 as the illumination unit information. In this case, the control circuit 8 compares this optical characteristic information with optical characteristic information regarding primary light transmission in the light port on the side of the light source unit 2 stored in the storage 8a of the control circuit 8. When determining that the primary light is transmittable by the result of the comparison, the control circuit 8 permits the operation of the primary light source connected to the corresponding light port. That is, the control circuit 8 determines that the primary light is transmittable when the optical characteristics of the primary light transmission in the light port on the side of the light source unit 2 correspond to the optical characteristics of the primary light transmission in the light port on the side of the illumination unit 3. However, when the optical characteristics do not correspond, the control circuit 8 can also determine that the primary light is transmittable in the case of a combination having no problem, as described later.

For example, when the light port on the side of the illumination unit 3 is an optical fiber having a core diameter $\phi$ of 115 μm and the light port on the side of the light source unit 2 is an optical fiber having a core diameter $\phi$ of 50 μm, the optical coupling of the side of the light source unit 2 to the side of the illumination unit 3 is sufficient. Therefore, the control circuit 8 can determine that there is no problem, and permits the operation of the primary light source.

For example, when the light port on the side of the illumination unit 3 is an optical fiber having a core diameter $\phi$ of 105 μm and the light port on the side of the light source unit 2 is an optical fiber having a core diameter $\phi$ of 115 μm, the control circuit 8 determines that leakage light in the ports is in an allowable range. Therefore, in this case, the control circuit 8 also permits the operation of the primary light source.

Although the core diameter is shown here by way of example as the optical characteristics regarding the primary light transmission in the light port, it is also possible to show the position for the core center of the optical fiber, or NA, as the example of the optical characteristics.

Not only the information regarding the characteristics of the primary light necessary for the operation but also the kind of light converting member may be stored in the ROM 19 as the illumination unit information. In this case, the control circuit 8 stores, in the storage 8a, a table in which the kind of light converting member and the information (conditions of the primary light) regarding the characteristics of the primary light necessary for the operation of each light converting member are recorded. From the information on the kind of light converting member obtained from the ROM 19, the control circuit 8 obtains the characteristics of the primary light necessary for the operation of the light converting member from the table. The control circuit 8 then makes determinations as described in the first embodiment, and controls the primary light source.

As information, the control circuit 8 may have, in the storage 8a, the kind of light converting member with which each primary light source is compatible. From the kind of light converting member stored in the ROM 19, the control circuit 8 may determine whether the light converting member can be combined with the primary light source without temporary conversion to primary light characteristics.

Instead of the kind of light converting member, an identification sign unique to the illumination unit may be stored in the ROM 19 as the illumination unit information. In this case, the control circuit 8 may store, in the storage 8a, a table in which the identification sign unique to the illumination unit and the information (conditions of the primary light) regarding the characteristics of the primary light sources necessary for the operation of the light converting member are recorded.

Second Embodiment (Configuration)

Figure 5:
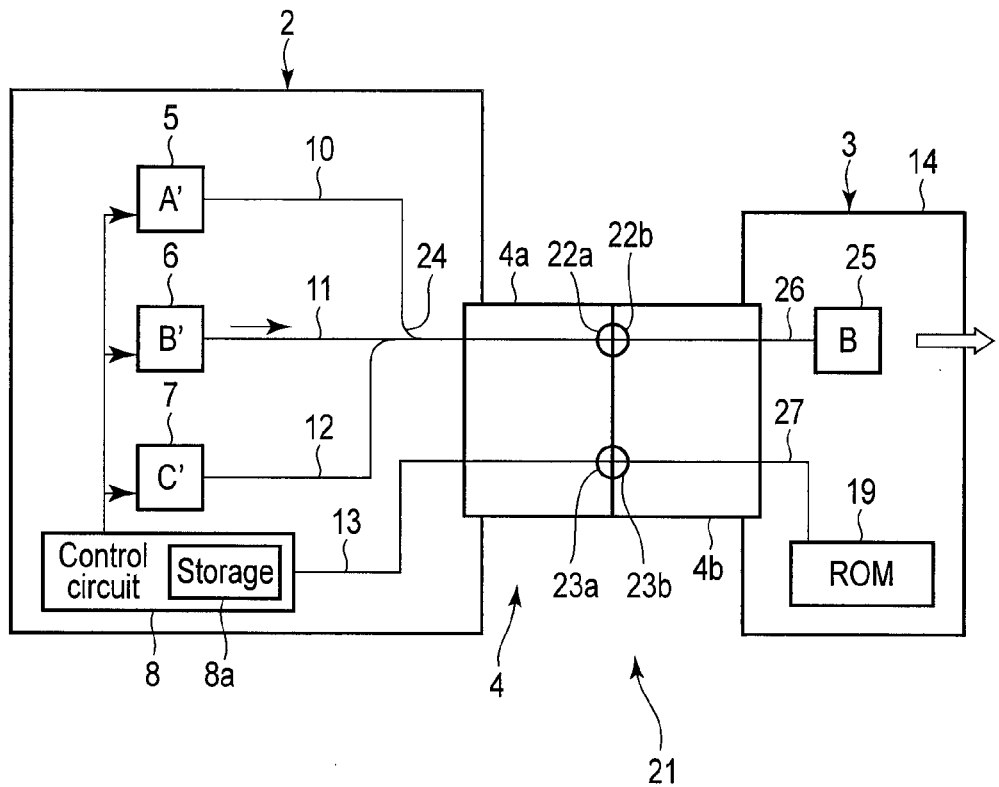
FIG. 5 is a schematic diagram showing the overall configuration of a light source device according to a second embodiment of the present invention.

FIG. 5 shows a second embodiment of the present invention. In the present embodiment, the configuration of the light source device 1 according to the first embodiment (see FIG. 1 to FIG. 4) is modified as follows. The same parts in FIG. 5 as those in FIG. 1 to FIG. 4 are provided with the same reference sings and are not described.

In a light source device 21 according to the present embodiment, one light connection light port 22a and one electric connection electric port 23a are provided in a first connector portion 4a connected on the side of the light source unit 2.

The light source unit 2 is provided with a light coupler (multiplexer) 24 which is a static switch that is turned under the on/off control of the three primary light sources (the first primary light source 5, the second primary light source 6, and the third primary light source 7) by the control circuit 8. Connected to the input terminal of the coupler 24 are the output end of the first optical fiber 10 connected to the first primary light source 5, the output end of the second optical fiber 11 connected to the second primary light source 6, and the output end of the third optical fiber 12 connected to the third primary light source 7. The output end of the coupler 24 is connected to the light port 22a of the first connector portion 4a. The control circuit 8 is connected to the electric port 23a of the first connector portion 4a via the electric signal line 13.

The second connector portion 4b connected to the side of the illumination unit 3 is provided with one light connection light port 22b and one electric connection electric port 23b. One light converting member 25 and the ROM 19 are mounted on the unit body 14 of the illumination unit 3.

One end of an optical fiber 26 is connected to the light converting member 25. The other end of the optical fiber 26 is connected to the light port 22b. Information regarding the characteristics (a maximum light output, a peak wavelength, and a spectrum shape) of the primary light necessary for the operation of the light converting member 25 connected to the light port 22b is stored in the ROM 19 as the illumination unit information. This ROM 19 is connected to the electric port 23b of the second connector portion 4b via an electric signal line 27.

(Functions)

Now, the functions of the above configuration are described. When the light source device 21 according to the present embodiment is used, the first connector portion 4a of the light source unit 2 is connected to the second connector portion 4b of the illumination unit 3. When the light source unit 2 and the illumination unit 3 are connected to each other, the electric port 23a of the first connector portion 4a is connected to the electric port 23b of the second connector portion 4b as shown in FIG. 5, so that the ROM 19 of the illumination unit 3 is connected to the control circuit 8 of the light source unit 2. In this condition, the control circuit 8 can read the information stored in the ROM 19 via the electric ports 23a and 23b of the connector 4 serving as the information transmitter.

The control circuit 8 then reads the illumination unit information including the characteristics (the maximum light output, the peak wavelength, and the spectrum shape) of the primary light necessary for the operation of the light converting member 25. In this instance, in the example shown FIG. 5, the control circuit 8 determines in accordance with the read illumination unit information that the second primary light source 6 can be combined with the light converting member 25, and the control circuit 8 permits the operation of the second primary light source 6 alone. In this way, the control circuit 8 controls so that the second primary light source 6 alone is switched to an active state and the other two primary light sources (the first primary light source 5 and the third primary light source 7) are switched to an inactive state. Thus, laser light is only emitted from the second primary light source 6 of the light source unit 2, and guided to the light converting member 25 via the second optical fiber 11 on the side of the light source unit 2, the light coupler 24, the light port 22a of the first connector portion 4a, the light port 22b of the second connector portion 4b, and the optical fiber 26 on the side of the illumination unit 3 in turn. The primary light received by the light converting member 25 is converted to secondary light and then radiated. The light radiated by the light converting member 25 is radiated to the outside as illumination light from the end face of the illumination unit 3. Thus, in this example, the primary light of the laser light radiated from the second primary light source 6 of the light source unit 2 is optically converted to secondary light by the light converting member 25 on the side of the illumination unit 3 and then radiated to the outside as illumination light.

If the illumination unit information indicating that the first primary light source 5 on the side of the light source unit 2 is suited to the light converting member 25 is read when the light source unit 2 and the illumination unit 3 are connected to each other, the control circuit 8 only permits the operation of the first primary light source 5. That is, in this case, the control circuit 8 controls so that the first primary light source 5 alone is switched to an active state and the other two primary light sources (the second primary light source 6 and the third primary light source 7) are switched to an inactive state. Thus, laser light is only emitted from the first primary light source 5 of the light source unit 2, and guided to the light converting member 25 via the first optical fiber 10 on the side of the light source unit 2, the light coupler 24, the light port 22a of the first connector portion 4a, the light port 22b of the second connector portion 4b, and the optical fiber 26 on the side of the illumination unit 3 in turn. Thus, in this example, the primary light of the laser light emitted from the first primary light source 5 of the light source unit 2 is optically converted to secondary light by the light converting member 25 on the side of the illumination unit 3 and then radiated to the outside as illumination light.

If the illumination unit information indicating that the third primary light source 7 on the side of the light source unit 2 is suited to the light converting member 25 is read when the light source unit 2 and the illumination unit 3 are connected to each other, the control circuit 8 only permits the operation of the third primary light source 7. That is, in this case, the control circuit 8 controls so that the third primary light source 7 alone is switched to an active state and the other two primary light sources (the first primary light source 5 and the second primary light source 6) are switched to an inactive state.

Thus, laser light is only emitted from the third primary light source 7 of the light source unit 2, and guided to the light converting member 25 via the third optical fiber 12 on the side of the light source unit 2, the light coupler 24, the light port 22a of the first connector portion 4a, the light port 22b of the second connector portion 4b, and the optical fiber 26 on the side of the illumination unit 3 in turn. Thus, in this example, the primary light of the laser light emitted from the third primary light source 7 of the light source unit 2 is optically converted to secondary light by the light converting member 25 on the side of the illumination unit 3 and then radiated to the outside as illumination light.

(Advantageous Effects)

Accordingly, in addition to the advantageous effects according to the first embodiment described above, the present embodiment has the following advantageous effects: The first connector portion 4a on the side of the light source unit 2 can be reduced in size owing to the configuration in which the light coupler 24 is provided on the side of the light source unit 2 and one light port 22a is only provided in the first connector portion 4a of the connector 4.

More than one light port 22a may be provided in the first connector portion 4a of the connector 4, and more than one corresponding light port 22b may be provided in the second connector portion 4b. In this case, the first connector portion 4a of the connector 4 may have a mixture of the light port 22a which can switch more than one primary light source and output and the light port which cannot switch the primary light sources.

Third Embodiment (Configuration)

Figure 6:
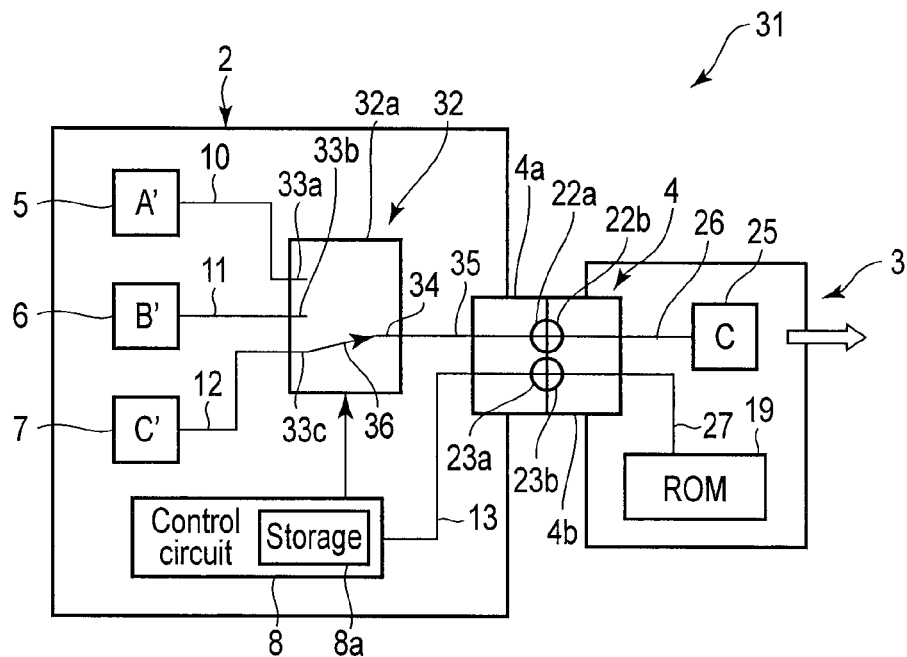
FIG. 6 is a schematic diagram showing the overall configuration of a light source device according to a third embodiment of the present invention.

FIG. 6 shows a third embodiment of the present invention. In the present embodiment, the light source device 21 according to the second embodiment (see FIG. 5) is modified as follows. The same parts in FIG. 6 as those in FIG. 5 are provided with the same reference sings and are not described.

In a light source device 31 according to the present embodiment, a dynamic switch 32 is provided instead of the light coupler 24 on the side of the light source unit 2 according to the second embodiment. The dynamic switch 32 switches the connection between the three primary light sources (the first primary light source 5, the second primary light source 6, and the third primary light source 7) and a light port 22 of the first connector portion 4a by mechanically driving a mirror and a fiber.

In a switch body 32a of the dynamic switch 32, three light ports 33a, 33b, and 33c are provided on an input side, and one light port 34 is provided on an output side. Here, the output end of the first optical fiber 10 connected to the first primary light source 5 is connected to the first light port 33a. Similarly, the output end of the second optical fiber 11 connected to the second primary light source 6 is connected to the second light port 33b, and the output end of the third optical fiber 12 connected to the third primary light source 7 is connected to the third light port 33c.

One end of an optical fiber 35 is connected to the light port 34 on the output side of the switch body 32a. The other end of the optical fiber 35 is connected to the light port 22a of the first connector portion 4a. Further, a light path switch 36 is provided in the switch body 32a to switch the connection of the three light ports 33a, 33b, and 33c on the input side and the light port 34 on the output side. This light path switch 36 performs a light path switch operation in accordance with a control signal from the control circuit 8. Thus, in accordance with the control circuit 8, the switch body 32a is operated to switch to a first light path on which the first light port 33a is connected to the light port 34, a second light path on which the second light port 33b is connected to the light port 34, or a third light path on which the third light port 33c is connected to the light port 34.

(Functions)

Now, the functions of the above configuration are described. When the light source device 31 according to the present embodiment is used, the first connector portion 4a of the light source unit 2 is connected to the second connector portion 4b of the illumination unit 3. When the light source unit 2 and the illumination unit 3 are connected to each other, the electric port 23a of the first connector portion 4a is connected to the electric port 23b of the second connector portion 4b as shown in FIG. 6, so that the ROM 19 of the illumination unit 3 is connected to the control circuit 8 of the light source unit 2. In this condition, the control circuit 8 can read the information stored in the ROM 19 via the electric ports 23a and 23b of the connector 4.

The control circuit 8 then reads the illumination unit information including the characteristics (a maximum light output, a peak wavelength, and a spectrum shape) of the primary light necessary for the operation of the light converting member 25. In this instance, in the example shown FIG. 6, the illumination unit information indicating that the third primary light source 7 on the side of the light source unit 2 is suited to the light converting member 25 can be read. Here, in the present embodiment, the light path switch 36 performs the light path switch operation for the switch body 32a of the dynamic switch 32 in accordance with the control signal from the control circuit 8. In this instance, the light path switch 36 switches to the third light path on which the third light port 33c is connected to the light port 34. The control circuit 8 only operates the third primary light source 7 of the light source unit 2.

Thus, laser light is emitted from the third primary light source 7 of the light source unit 2, and guided to the light converting member 25 via the third optical fiber 12 on the side of the light source unit 2, the light path switch 36 of the dynamic switch 32, the optical fiber 35, the light port 22a of the first connector portion 4a, the light port 22b of the second connector portion 4b, and the optical fiber 26 on the side of the illumination unit 3 in turn. Thus, in this example, the primary light of the laser light emitted from the third primary light source 7 of the light source unit 2 is optically converted to secondary light by the light converting member 25 on the side of the illumination unit 3 and then radiated to the outside as illumination light.

In this case as well, if the illumination unit information indicating that the first primary light source 5 on the side of the light source unit 2 is suited to the light converting member 25 is read when the light source unit 2 and the illumination unit 3 are connected to each other, the control circuit 8 switches the light path switch 36 of the switch body 32a of the dynamic switch 32 to the first light path on which the first light port 33a is connected to the light port 34. Thus, in this example, the primary light of the laser light radiated from the first primary light source 5 of the light source unit 2 is optically converted to secondary light by the light converting member 25 on the side of the illumination unit 3 and then radiated to the outside as illumination light.

If the illumination unit information indicating that the second primary light source 6 on the side of the light source unit 2 is suited to the light converting member 25 is read when the light source unit 2 and the illumination unit 3 are connected to each other, the control circuit 8 switches the light path switch 36 of the switch body 32a of the dynamic switch 32 to the second light path on which the second light port 33b is connected to the light port 34. Thus, in this example, the primary light of the laser light emitted from the second primary light source 6 of the light source unit 2 is optically converted to secondary light by the light converting member 25 on the side of the illumination unit 3 and then radiated to the outside as illumination light.

(Advantageous Effects)

Accordingly, advantageous effects similar to those according to the second embodiment can also be obtained in the present embodiment.

It should be noted that the present invention is not limited to the embodiments described above. For example, in the case of the dynamic switch 32 according to the third embodiment, a static actuator, an electromagnetic actuator, or a piezoelectric actuator may be used as a driving member. A depression/projection portion may be provided in the second connector portion 4b of the connector 4 on the side of the illumination unit 3, and when the first connector portion 4a of the light source unit 2 of the connector 4 is connected to the second connector portion 4b of the illumination unit 3, the depression/projection portion may mechanically operate the light path switch 36 of the dynamic switch 32 and switch the optical paths. In this case, the depression/projection portion serves as the illumination unit information.

Furthermore, it should be appreciated that various modifications can be made without departing from the spirit of the present invention.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A light source device comprising:
   a light source unit configured to emit primary light;
   an illumination unit configured to optically convert the primary light to secondary light and then emit the secondary light;
   a connector configured to allow the light source unit and the illumination unit to be attached to and detached from each other; and
   an information transmitter configured to transmit illumination unit information to the light source unit, the illumination unit information being information regarding the illumination unit.

2. The light source device according to claim 1, wherein the light source unit includes:
   a primary light source configured to emit primary light; and
   a control circuit configured to control the emission of the primary light from the primary light source in accordance with the illumination unit information obtained via the information transmitter, the illumination unit includes a light converting member configured to receive the primary light emitted from the primary light source, convert the primary light to secondary light, and emit the secondary light as illumination light, and the connector is provided with a port configured to pass, to the light converting member, the primary light emitted from the primary light source.

3. The light source device according to claim 2, wherein the illumination unit information includes one of information regarding the primary light convertible by the light converting member of the illumination unit, and optical information regarding primary light transmission in the port, and the information transmitter transmits the illumination unit information to the light source unit via the connector.

4. The light source device according to claim 3, wherein the light source unit includes more than one primary light source, the connector includes more than one port, the illumination unit information is individually present for at least some of the ports, and the control circuit controls each of the primary light sources connected to the ports in accordance with the illumination unit information.

5. The light source device according to claim 4, wherein the illumination unit information includes information regarding whether the light converting member is connected to each of the ports, and the control circuit prohibits the output of the primary light source connected to the port when the light converting member is not connected to the port.

6. The light source device according to claim 4, wherein the illumination unit information includes a condition of primary light convertible by the light converting member connected to each of the ports, and the control circuit permits the output of the primary light source when the primary light source connected via the port satisfies the condition of the primary light.

7. The light source device according to claim 6, wherein the condition of the primary light is an allowable incident light intensity, and the control circuit controls to keep an output light intensity of the primary light source below the allowable incident light intensity.

8. The light source device according to claim 6, wherein the condition of primary light is one of an absorption spectrum of the primary light necessary for the operation of the light converting member, and a peak wavelength of the absorption spectrum.

9. The light source device according to claim 6, wherein the illumination unit is configured so that the light converting members simultaneously operate, the illumination unit information is a light intensity ratio which is a ratio among light intensities of the primary light to enter the light converting members necessary to obtain desired illumination light, and the control circuit controls an output light intensity of the primary light source connected to each port to maintain the light intensity ratio.

10. The light source device according to claim 4, wherein the illumination unit includes more than one light converting member connected to more than one port, the illumination unit information includes a condition of primary light convertible by the light converting member connected to each of the ports, and the control circuit controls the primary light source connected via the port to satisfy the condition of the primary light.

11. The light source device according to claim 4, wherein the illumination unit information includes optical information regarding primary light transmission in each port on the side of the illumination unit, and when the primary light is determined to be transmittable by information regarding the port on the side of the light source unit, the output of the primary light source connected to the port is permitted.

12. The light source device according to claim 4, wherein the illumination unit information is the kind of each of the light converting members connected to the ports, the light source unit includes a first table in which the kind of light converting member and a condition of primary light necessary for the operation of the light converting member are recorded, and the light source unit finds a condition of the convertible primary light from the kind of light converting member in accordance with the illumination unit information and the first table, and controls the output of the primary light source.

13. The light source device according to claim 4, wherein the illumination unit information is an identification sign unique to the illumination unit, the light source unit includes a second table in which the identification sign unique to the illumination unit and a condition of primary light necessary for the operation of the illumination unit are recorded, and the light source unit finds a condition of the primary light convertible by the light converting member connected to each of the ports from the unique identification sign in accordance with the illumination unit information and the second table, and controls the output of the primary light source in accordance with the condition of the primary light.

14. The light source device according to claim 2, wherein the illumination unit information includes one of mechanical information and thermal information regarding the illumination unit, and the information transmitter transmits the illumination unit information to the light source unit via the connector.

15. The light source device according to claim 2, wherein the light source unit is configured to switch and output more than one kind of primary light having different characteristics from the port.

16. The light source device according to claim 2, wherein when the information is not acquired, the control circuit does not permit the operation of the light source unit.

17. The light source device according to claim 2, wherein the light source unit includes an informer, and the control circuit uses the informer to inform one of a function usable as the light source device, a state that the output of the primary light source is not permitted, and a state that the output of the primary light source is prohibited, in accordance with one of the illumination unit information, information regarding the primary light source mounted on the light source unit, and the permission of the output of the primary light source.

* * * * *